United States Patent [19]
Brockhoff

[11] Patent Number: 5,824,212
[45] Date of Patent: Oct. 20, 1998

[54] CYCLONE APPARATUS FOR REMOVAL OF AIR FROM AIR CONTAINING BLOOD

[75] Inventor: Alexander Brockhoff, Fürstentum, Liechtenstein

[73] Assignee: Kevin Business Corporation, Obarrio, Panama

[21] Appl. No.: 571,490

[22] Filed: Dec. 13, 1995

[30] Foreign Application Priority Data

Dec. 6, 1995 [DE] Germany .................. 195 45 404.9

[51] Int. Cl.[6] ............... B01D 21/26; B01D 19/00
[52] U.S. Cl. ............ 210/194; 210/512.1; 210/188; 55/459.1; 96/209; 96/155; 604/5
[58] Field of Search ............... 210/512.1, 188, 210/782, 194; 55/459.1; 604/5; 96/204, 155

[56] References Cited

U.S. PATENT DOCUMENTS

| | | |
|---|---|---|
| 3,785,380 | 1/1974 | Brumfield . |
| 4,368,118 | 1/1983 | Siposs . |
| 4,388,922 | 6/1983 | Telang ............... 604/319 |
| 5,451,321 | 9/1995 | Matkovich . |

FOREIGN PATENT DOCUMENTS

| | | |
|---|---|---|
| 3641644 | 1/1987 | Germany . |
| 3624363 | 1/1988 | Germany . |
| 4329385 | 3/1995 | Germany . |
| 2063108 | 9/1980 | United Kingdom . |

OTHER PUBLICATIONS

Search Report EP 96 11 8573.

*Primary Examiner*—David A. Reifsnyder
*Attorney, Agent, or Firm*—Ostrolenk, Faber, Gerb & Soffen, LLP

[57] ABSTRACT

A method and apparatus for removing air from blood which contains air. The air-containing blood is conducted in the form of a cyclone stream through a cyclone device, preferably drawn therethrough, so that centrifugal forces for the separation of the air from the blood are produced in the rotating cyclone stream.

21 Claims, 5 Drawing Sheets

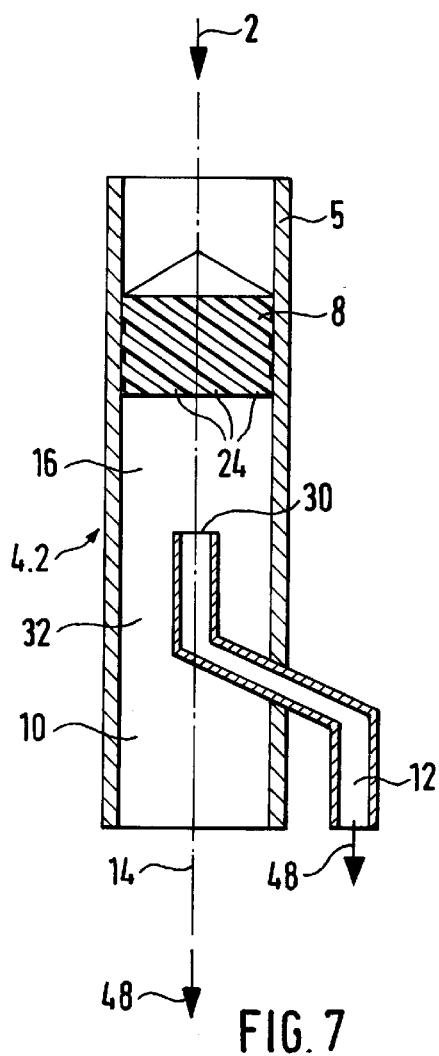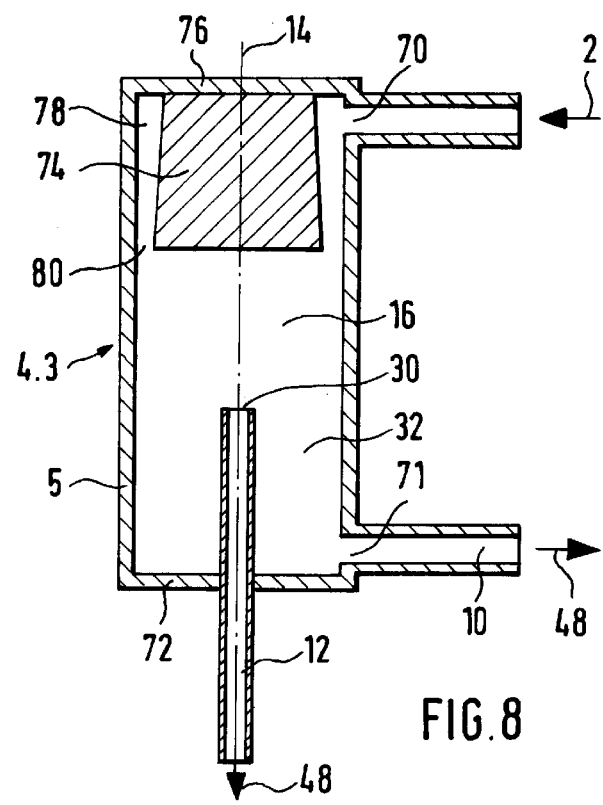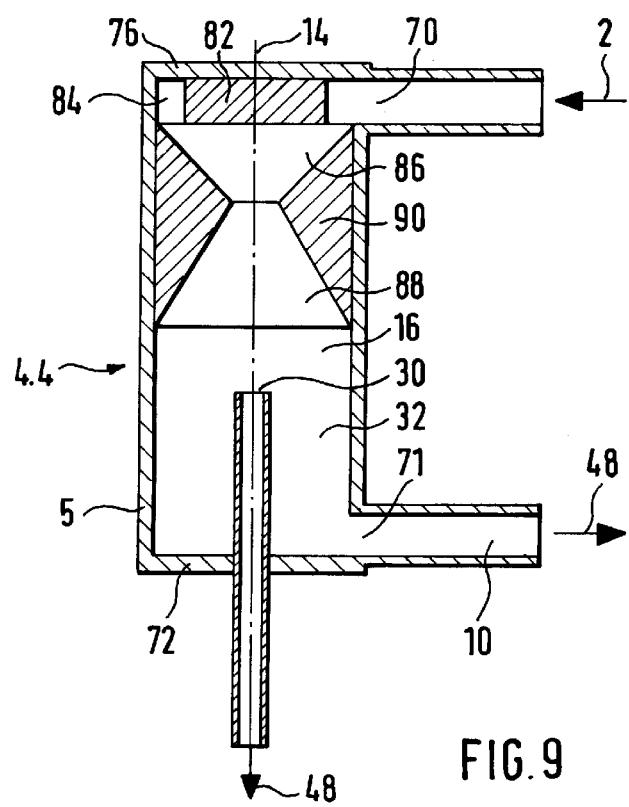
FIG. 7
FIG. 8
FIG. 9

CYCLONE APPARATUS FOR REMOVAL OF AIR FROM AIR CONTAINING BLOOD

The present invention relates to a process and an apparatus for removing air from air-containing blood in accordance with the independent claims.

The invention relates, in particular, to the removal of air from a flowing stream of blood which is drawn off from a patient, for instance from a wound or place of operation, or from a blood-container of a blood-donor device.

Upon the drawing off of blood, for instance from a patient during an operation, air is frequently also drawn in from the environment. The air mixes with the blood and leads to damage to the components of the blood. In this way, treatment and reuse of the blood is made difficult.

In actual practice today, blood is drawn off from the operating wound of a patient by systems which consist of a cannula, a conveyor system in the form of a roller pump or a vacuum pump, a blood recirculation system, and connecting lines. These known systems extensively traumatize (damage) the blood.

The reasons for the traumatizing of the blood by the known systems are, among others, the following:

1. The active drawing off of blood from the operating region of a patient results in an intense mixing of the liquid phase (blood) with the gaseous phase (air). This mixing takes place not only at and in the suction cannula but also in the connecting lines, and it constitutes the main factor for the traumatizing of the blood.
2. In order to achieve an effective drawing-off of the blood, the known systems require a relatively high vacuum, which causes additional damage to the components of the blood.

More recent systems for the drawing off of blood are therefore developed in such a manner that they can separate the gaseous phase from the liquid phase so as to limit the damage done to the blood. The known systems are, however, bulky, large, heavy, difficult to operate, and expensive to manufacture. One such system is known, for instance, from U.S. Pat. No. 4,388,922.

The object of the invention is to create a blood-air separation system which has a less traumatic effect on blood and with which even micro-small air bubbles can be removed from a flowing stream of blood.

The invention is of particular advantage in operations with heart-lung machines, liver transplants, many other operations in body cavities and, in general, in the case of blood donations with a blood oxygenator.

Furthermore, the system in accordance with the invention is to be so developed that air present in the blood drawn off can be removed from the blood shortly behind the place where the blood is drawn off, and in particular close to the patient. The system is to be of low cost and easy to use. The system of the invention is to make the following possible:

1. Maximum separation of the gaseous phase (air), even if it consists of small air bubbles of a diameter of only a few $\mu$m, from the liquid phase (blood), preferably immediately and directly at or close to the place where the blood is drawn off;
2. A reduction in the vacuum necessary for the drawing off.

This object is achieved in accordance with the invention by the independent claims.

In accordance with the invention, the blood is placed in an eddying movement in a cyclone, so that the heavy components of the blood-air mixture are forced radially outward by centrifugal force while the physically lighter components and thus, in particular, the air are forced into the radial center of the cyclone eddy stream. By separate drawing off of the radially outwardly forced liquid phase and of the gaseous phase forming radially within it, the gaseous phase is separated from the liquid phase.

In the present specification and the drawings, only embodiments with one cyclone are shown. However, it is clear to the person skilled in the art that several cyclones in parallel or in series can also be used. The following description of a cyclone is therefore representative of embodiments having several cyclones used in parallel or in series.

In one preferred embodiment of the invention, the cyclone is arranged in a small handle part of a blood-suction cannula. This has the advantage that the air is separated from the blood directly behind the place of removal of the blood and that the cyclone is in a position which is favorable from a standpoint of weight. The cyclone can be integrated into the blood-suction cannula or be arranged at the downstream end of the blood-suction cannula. The outer wall of the cannula and/or of the handle part preferably at the same time forms the outer wall of the cyclone.

Further features of the invention are set forth in the dependent claims.

The invention will be described below with reference to the drawings on the basis of several preferred embodiments as examples. In the drawings:

FIG. 7 is a diagrammatic axial section through another embodiment of a cyclone in accordance with the invention, similar to FIG. 1;

FIG. 8 shows diagrammatically an axial section through another embodiment of a cyclone in accordance with the invention;

FIG. 9 shows diagrammatically an axial section through another embodiment of a cyclone for the separating of air from a flowing stream of blood in accordance with the invention;

Figure 1:
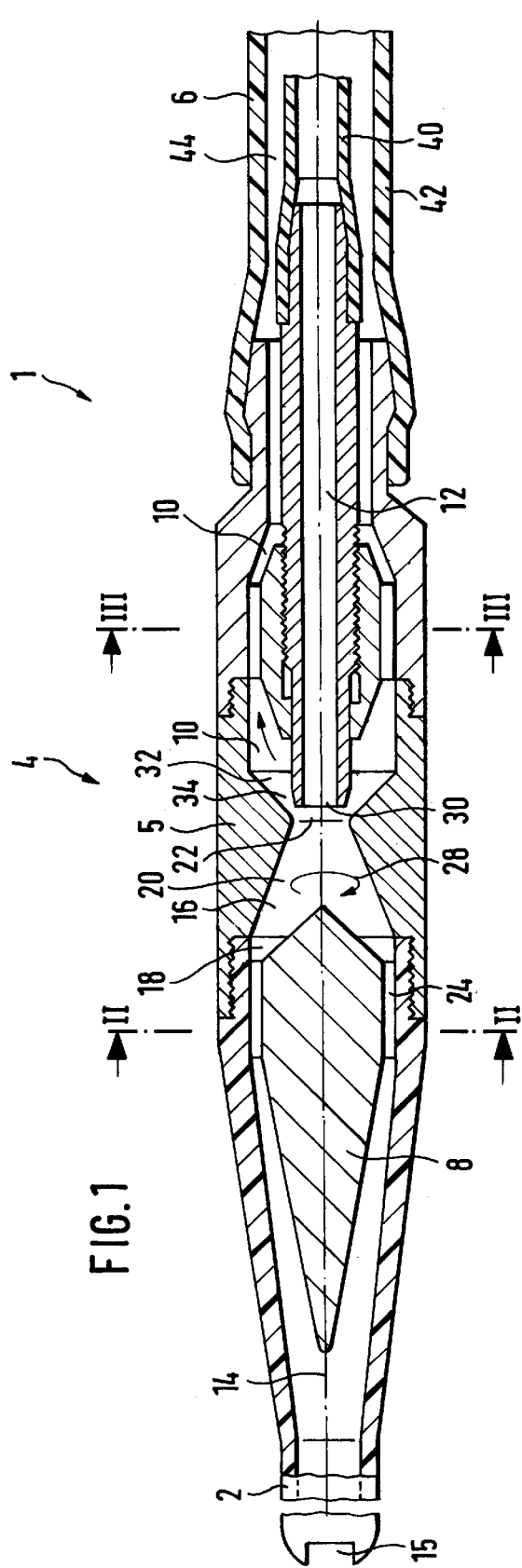
FIG. 1 is an axial longitudinal section through a blood-suction device in accordance with the invention, on a scale of 4:1.
Figure 4:
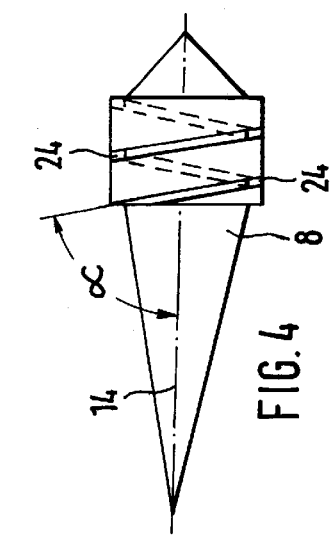
FIG. 4 is a side view of a flow body of the blood-suction device of FIG. 1.
Figure 3:
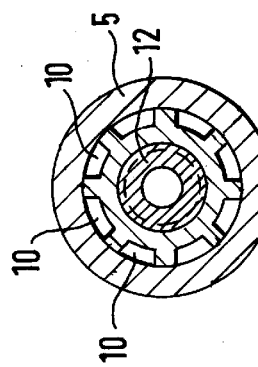
FIG. 3 is a cross section along the plane III—III of FIG. 1.
Figure 2:
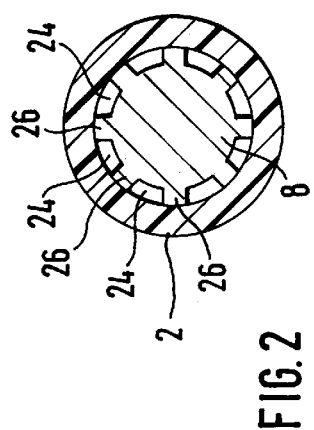
FIG. 2 is a cross section along the plane II—II of FIG. 1.

The blood-suction device 1 of FIGS. 1 to 4 consists of a blood-suction cannula 2, a cyclone device 4 on the downstream end of the blood-suction cannula 2, and a double hose or double lumen 6 on the downstream end of the cyclone device 4. The cyclone device 4 contains, within an outer wall 5, a flow guide body 8, a liquid channel 10 of annular cross section, and a gas channel 12 arranged axially in the radial center therein. All parts are arranged axially to a center axis 14. The cyclone wall 5 forms a handle for the blood-suction cannula 2 and can consist of one piece with the blood-suction cannula or, as shown in the drawings, of several parts which can be connected detachably to each other. The blood-suction cannula 2 has a suction inlet 15 on its upstream end. The wall 5 forms a cyclone eddy chamber 16 which consists of an upstream cylindrical section 18 and an adjoining nozzle section 20 which narrows in funnel shape in the direction of flow and has a nozzle opening 22 in the radial center. Helical grooves 24 between helical ribs 26 of the flow-guide body 8 and the cyclone wall 5 resting against them form an "approximately tangential" cyclone inlet on the upstream starting end of the cyclone eddy chamber 16. The expression "approximately tangential" means here a direction which extends precisely in tangential direction 90° to the middle axis 14 or at least so obliquely to the center axis 14 that the axial blood-air-mixture suction stream of the blood-suction cannula 2 in the cyclone eddy chamber 16 flows as eddy stream 28 in circumferential direction along the cyclone wall 5, thereby producing centrifugal forces which drive the blood components (liquid phase) of the mixture suction stream radially outward to the wall 5 and thereby separate them from the radially inwardly displaced air (gaseous phase) of the mixture suction stream. The nozzle section 20 which narrows down in funnel shape produces a reduction in the available cross section of flow and thus in an increase in the velocity of flow of the suction stream in circumferential direction.

The gas inlet 30 of the gas channel 12 forms the gas outlet of the cyclone eddy chamber 16 and has a smaller cross section than the nozzle opening 22 and is located only a short distance away, downstream from said nozzle opening 22. The liquid inlet 32 of the liquid channel 10 forms the blood outlet of the cyclone eddy chamber 16 and is formed in ring-shape between the gas inlet 30 of the gas channel 12 and a diffusor channel section 34 which widens in cross section in funnel shape in the direction of flow and follows behind the nozzle opening 22. The gas channel 12 and its gas inlet 30 consist of a tube which is replaceably inserted into the cyclone wall 5. The cyclone nozzle section 20 which narrows down in funnel shape results in an acceleration of the flow and the diffusor channel 31 which widens in funnel shape and follows it effects a slowing down of the cyclone eddy stream. By this combination, better efficiency is obtained in the separation of air and blood.

Figure 5:
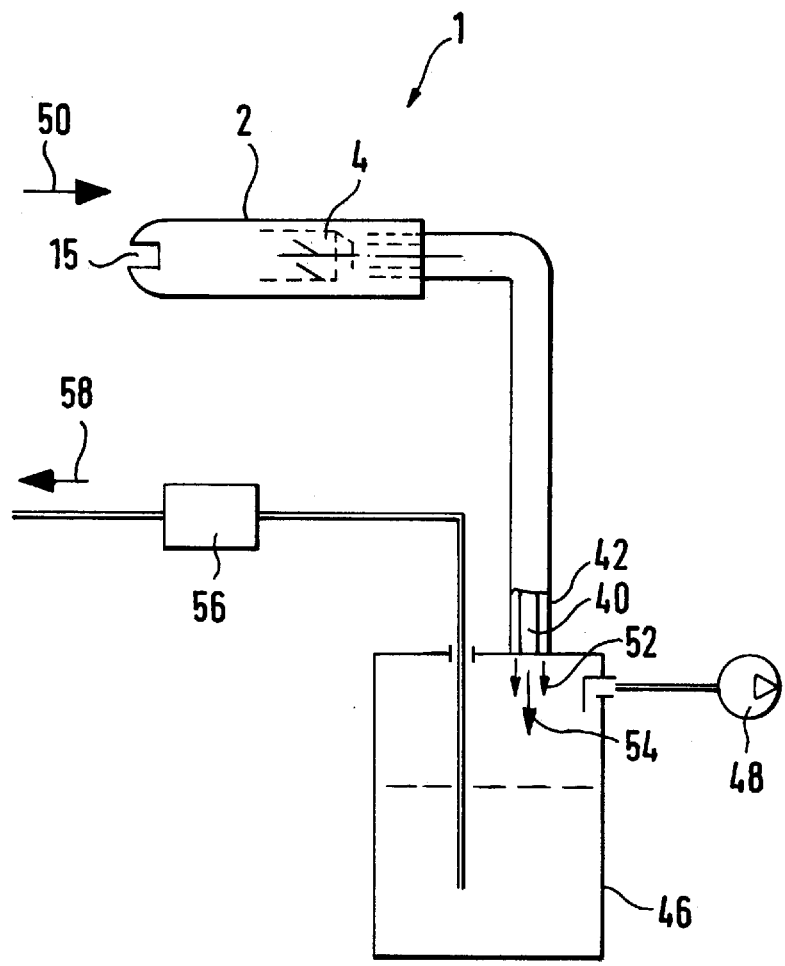
FIG. 5 shows diagrammatically the use of a blood-suction device in accordance with FIG. 1 in a system for the drawing off of blood from a patient, treatment of the blood and recirculation of the blood back to the patient.
Figure 6:
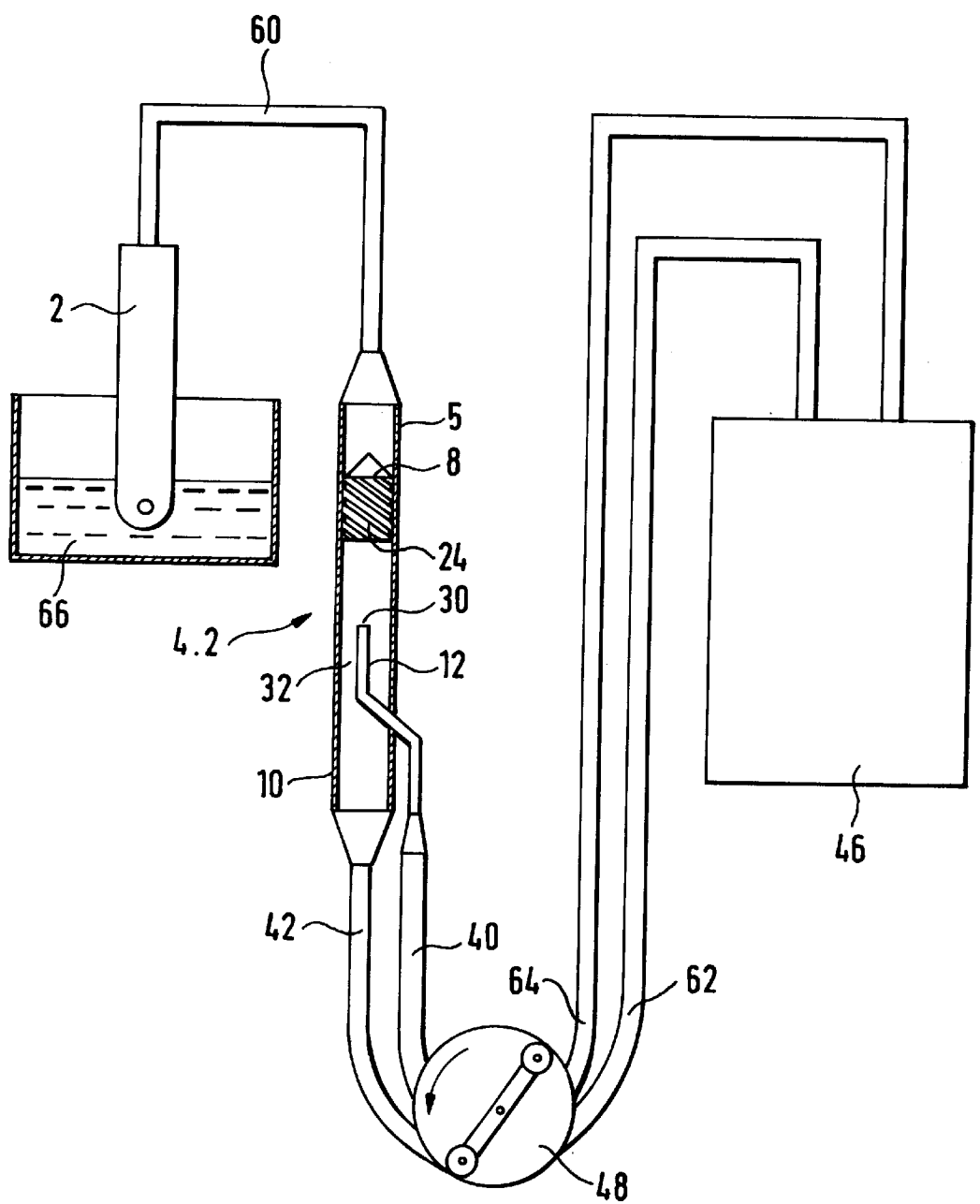
FIG. 6 shows diagrammatically another embodiment of the blood-suction device in accordance with the invention.

The double hose 6 consists of a radially inner hose 40 which is connected to the downstream end of the tube of the gas channel 12 and of a radially outer tube 42 which surrounds the inner hose 40 spaced radially from it and is connected to the downstream end of the cyclone wall 5 in such a manner that the liquid channel 10 is in flow communication with the space 44 which is formed between the two tubes 40 and 42. The two tubes 40 and 42 are connected at their downstream ends (not shown) to a source of suction 48 either directly, as shown in FIG. 6, or with the interpositioning of the blood reservoir 46, as shown in FIG. 5. The grooves 24 in the flow guide body can have a varying angle of slope alpha of from approximately zero degrees on the upstream starting end to about ninety degrees at the downstream end, with reference to the middle axis 14 in accordance with FIG. 4.

FIG. 5 diagrammatically shows the blood-suction device 1 which draws blood and air in the direction of an arrow 50 from a wound, for instance an operating wound, through the suction inlet 15 of the blood-suction cannula 2, separates the blood-air-mixture suction stream in the cyclone device 4 into a blood phase 52 and a gaseous phase 54 and draws both phases 52 and 54 into the blood reservoir 46. The suction source 48 is connected to the blood reservoir 46 above its liquid level. The blood can be recirculated from the blood reservoir 46 via a blood-treatment and blood-conveying device 56 in the direction indicated by an arrow 58 back into the circulation of the patient or be introduced into blood banks.

In the embodiment shown in FIG. 6, the source of suction 48 is a roller pump which is arranged in the path of flow between another embodiment of a cyclone device 4.2 and the blood reservoir 46. The blood-suction cannula 2 can be connected in an arc or via a short connecting tube 60 to the upstream end of the cyclone device 4.2. The downstream end of the cyclone device 4.2 is connected by the two tubes 40 and 42 to the suction side of the roller pump 48. The delivery side of the roller pump 48 is connected via a tube 62 for the liquid phase (blood) and a separate tube 64 for the gaseous phase (air) to the blood reservoir 46. The patient 66 is indicated merely diagrammatically in the form of a blood vessel.

The cyclone device 4.2 of FIG. 6 which is shown in FIG. 7 contains a flow body 8 the upstream end of which has the shape of a cone of short cone height and the downstream end of which is flat. The cyclone eddy chamber 16 is of a circular cylindrical shape over its entire axial length. The gas inlet 30 of the gas channel 12 is arranged in the radial center of the eddy stream 28 produced by the flow guide body 8. The gas channel 12 is extended laterally out of the cyclone eddy chamber 16 downstream of its inlet 30 so that, in this embodiment, the two hoses 40 and 42 are not coaxial to each other but lie outside of one another.

In the embodiments described above, the middle axis 14 extends horizontally, vertically or obliquely in the cyclone device 4 or 4.2 depending on the position of the operator.

The embodiments of cyclone devices 4.3 and 4.4 shown in FIGS. 8 and 9 can be placed as independent units on a base so that the middle axis 14 of the cyclone devices 4.3 and 4.4 is vertical. Each of the cyclone devices 4.3 of FIG. 8 and 4.4 of FIG. 9 has a circular cylindrical cyclone wall 5; on the upper, upstream end of the wall 5 a tangential cyclone inlet 70 which is connected to a blood-suction cannula 2, not shown; at the lower, downstream end of the wall 5, a tangential first cyclone outlet 71 which is a part of the liquid channel 10 the inlet 32 of which is formed by the annular space between the cyclone wall 5 and the gas channel 10; a second cyclone outlet in the form of the inlet 30 of the gas channel 12 which extends through an eddy-chamber bottom 72 so that the inlet 30 of the gas channel 12 is arranged in the radial cyclone center of the eddy chamber 16 upstream of the liquid inlet 32 of the liquid channel.

In the embodiment shown in FIG. 8, there is present in the cyclone eddy chamber 16 a conical insert body 74 which extends from an eddy-chamber cover 76 above the cyclone inlet 70 past the cyclone inlet 70 and forms, between itself and the cyclone wall 5, an annular nozzle channel 78 concentric to the middle axis 14 which narrows in wedge shape from the cyclone inlet 70 to an annular nozzle opening 80 and thereby accelerates the blood-air-mixture suction stream. The downstream side of the insert body 74 is flat at a right angle to the middle axis 14 and is spaced from the inlet 30 of the gas channel 12.

The cyclone device 4.4 of FIG. 9 is provided on the inner side of its eddy-chamber cover 76 with a circular-cylindrical insert body 82. The insert body 82, together with the cyclone wall 5, forms an annular chamber 84 in the region of the cyclone inlet 70. The annular chamber 84 is followed, in direction of flow, along the middle axis 14 by a nozzle section 86 which narrows down in funnel-like manner and then by a diffusor section 88 which widens in funnel shape and is located with axial spacing axially opposite the inlet 30 to the gas channel 12. The nozzle section 86 and the diffusor section 88 are formed by a second insert body 90 which is inserted into the cyclone wall 5.

The cyclone devices of the invention form a "dynamic air separator" since it is traversed by the blood and in this connection removes air from the blood. The cyclone devices still have a good air-separation efficiency even in the case of very small amounts of blood and very small air bubbles of a size of only a few μm.

Figure 10:
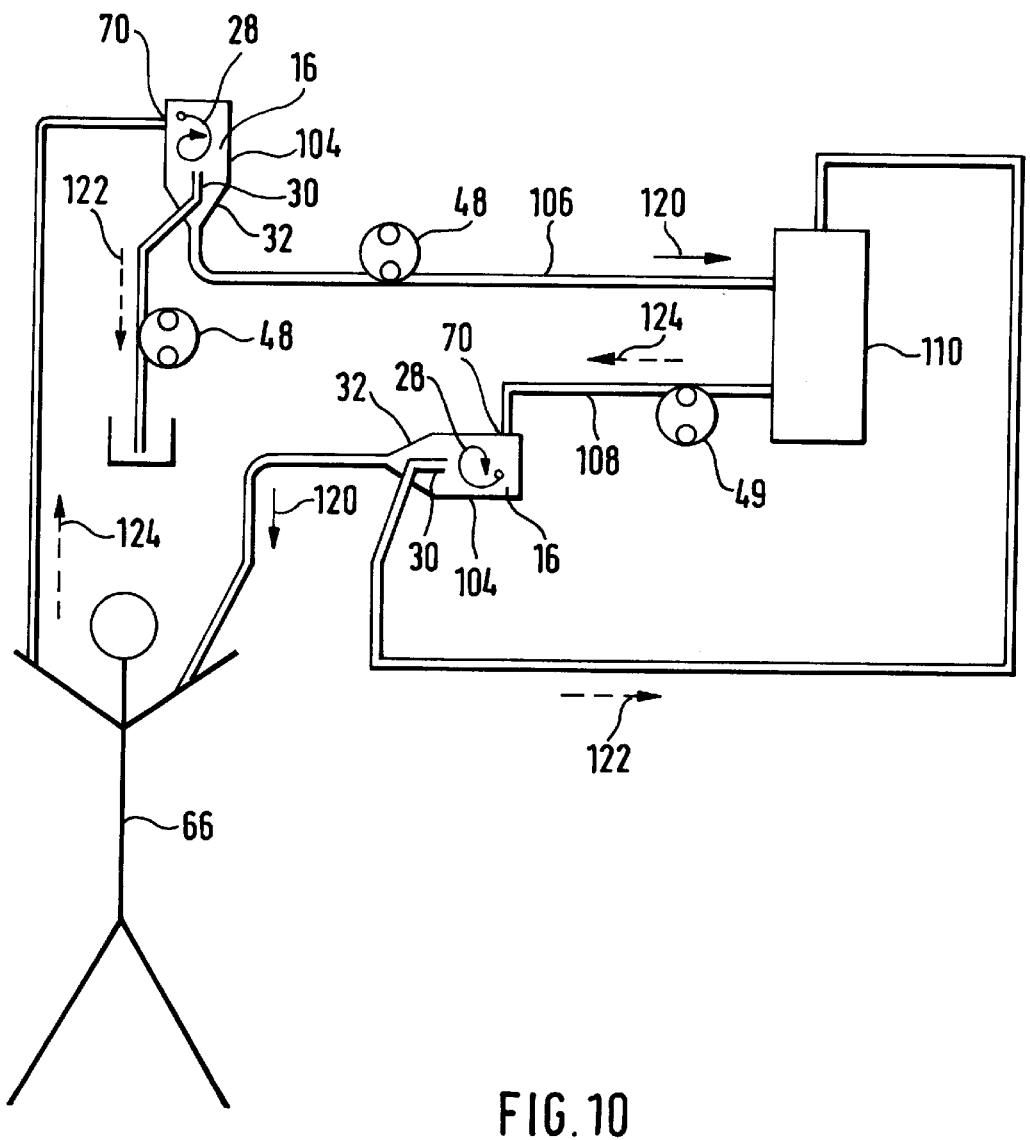
FIG. 10 shows diagrammatically a device in accordance with the invention for the separating of air from a flowing stream of blood both in forward passage and in return passage between a patient and a blood-treatment device, for instance a heart-lung machine, which has an oxygenator for the enriching of oxygen in the blood.

The device in accordance with the invention which is shown in FIG. 10 contains a cyclone 104 in the forward travel path 106 and a cyclone 104 in the return travel path 108 of a blood circulation from a patient 66 to a heart-lung machine 110 which contains an oxygenator for enriching the oxygen in the blood, and back again to the patient 66. For the drawing off of the blood from the patient 66, there is a pump 48 in the forward path 106 between its cyclone 104 and the heart-lung machine 110. The gaseous phase can be drawn from the cyclone 104 of the forward path 106 by a separate flow path of the same pump or by a second pump 48.

In the return travel 108, there is a pump 49 between the heart-lung machine 110 and its cyclone 104. In this case, the blood is not drawn through this cyclone 104 but driven through it. The gaseous phase of this cyclone 104 in the return path 108 can be returned by the conveying force of the pump 104 into the heart-lung machine 110.

The cyclones 104 of the forward path 106 and the return path 108 have a tangential inlet 70 at one axial end of a circular cyclone eddy chamber and, at their other, axial end, a blood outlet 32 at the cyclone-chamber wall and an air outlet 30 in the radial center of the cyclone eddy chamber 16.

The forward path 106 and the return path 108 form two different processes which can be used separately from each other or, in accordance with FIG. 10, in combination with each other. The cyclone 104 in the forward path 106 serves for the separating of air drawn off, undesired, from the patient from the blood which is drawn off at the same time from the patient. The cyclone 104 in the return path 108 serves for the separating of very small air bubbles of a diameter within the μm range which pass in the oxygenator of the machine 110 into the blood which is conveyed to the patient.

In accordance with an embodiment which is not shown in the drawing, the pump 48 in the forward path can be omitted and its suction action produced by the pump 49 of the return path 108 through the machine 110. In FIG. 10, the solid line arrows 120 indicate the direction of flow of the blood and the dashed-line arrows 122 the direction of flow of the air, while the combined solid-dashed lines 124 indicate the direction of flow of the blood-air mixture.

The blood-suction place can be a wound, an operating site or any desired blood vessel of a patient 66, or a container, for instance a blood bank, or a machine, for instance a heart-lung machine 100 and/or an oxygenator for the enrichment of the oxygen in the blood.

I claim:

1. A cyclone device for removing gas from blood, the blood having a blood phase and a gaseous phase, the cyclone device comprising:

a cyclone wall having an inner surface extending around a middle axis;

a cyclone eddy chamber defined by the inner surface of the cyclone wall, the chamber having an inlet at one axial end for receiving the blood and an outlet at an opposite axial end for the blood to exit;

a cyclone inlet being substantially tangentially directed and disposed at the inlet of the eddy chamber such that, when the blood passes through the eddy chamber, the blood phase forms a radial outer component and the gaseous phase forms a radial inner component of the blood;

a first cyclone outlet for removing the blood phase from the blood, the first cyclone outlet being formed by the inner surface of the cyclone wall at the outlet of the cyclone eddy chamber; and a second cyclone outlet for removing the gaseous phase from the blood, the second cyclone outlet being arranged coaxially within the first cyclone outlets.

2. The cyclone device of claim 1, further comprising a handle, the cyclone device being disposed within the handle.

3. The cyclone device of claim 1, wherein the cyclone eddy chamber narrows at a narrow end and the narrow end is proximate to both the first and second outlets cyclone.

4. The cyclone device of claim 3, further comprising:

a diffuser section having first and second axial ends, the first axial end communicating with the narrow end of the cyclone eddy chamber, the diffuser section widening at the second axial end and forming a part of the first cyclone outlet.

5. The cyclone device of claim 1, wherein the cyclone device is arranged in a flow path between a blood suction location and a suction source for drawing off the blood from the blood suction location, the cyclone device being substantially closer to the blood suction location than to the suction source.

6. The cyclone device of claim 5, further comprising a blood suction cannula communicating with the cyclone device to deliver the blood to the cyclone inlet.

7. The cyclone device of claim 1, further comprising a blood suction cannula communicating with the cyclone device to deliver the blood to the cyclone inlet.

8. The cyclone device of claim 7, wherein the cyclone eddy chamber narrows at a narrow end, and the narrow end is proximate to both the first and second cyclone outlets.

9. The cyclone device of claim 8, further comprising a diffuser section having first and second axial ends, the first axial end communicating with the narrow end of the cyclone eddy chamber, the diffuser section widening at the second axial end and forming a part of the first cyclone outlet.

10. The cyclone device of claim 1, wherein the cyclone inlet includes:

a flow guide body disposed forward of the eddy chamber; and helical ribs disposed on the flow guide body and forming helical grooves with the cyclone wall, the helical grooves being approximately tangential to the middle axis.

11. The cyclone device of claim 10, wherein the cyclone eddy chamber narrows at a narrow end, and the narrow end is proximate to both the first and second cyclone outlets.

12. The cyclone device of claim 11, further comprising a diffuser section having first and second axial ends, the first axial end communicating with the narrow end of the cyclone eddy chamber, the diffuser section widening at the second axial end and forming a part of the first cyclone outlet.

13. The cyclone device of claim 10, further comprising a blood suction cannula communicating with the cyclone device to deliver the blood to the cyclone inlet.

14. The cyclone device of claim 1, further comprising:

a conical flow guide body having an outer surface and being disposed at the cyclone inlet, the conical flow guide body forming an annular nozzle channel between the outer surface thereof and the inner surface of the cyclone wall, the annular nozzle channel being concentric with the middle axis of the cyclone eddy chamber, said channel narrowing in a wedge shape from the cyclone inlet toward the cyclone eddy chamber such that the stream of blood and air flowing from the cyclone inlet into the cyclone eddy chamber is accelerated.

15. The cyclone device of claim 14, wherein the flow guide body includes helical ribs disposed on the outer surface thereof and forming helical grooves with the inner surface of the cyclone wall, the helical grooves being approximately tangential to the middle axis.

16. A blood recirculation system for conditioning blood from a source, the blood having a blood phase and a gaseous phase, the recirculation system comprising:
 a cyclone device according to claim 1 for receiving the blood from the source and separating the gaseous phase from the blood phase; and
 a blood conditioning device for receiving the blood phase from the cyclone device, producing conditioned blood and returning the conditioned blood to the source.

17. The blood recirculation system of claim 16, wherein the cyclone eddy chamber narrows at a narrow end, and the narrow end is proximate to both the first and second cyclone outlets.

18. The blood recirculation system of claim 17, further comprising a diffuser section having first and second axial ends, the first axial end communicating with the narrow end of the cyclone eddy chamber, the diffuser section widening at the second axial end and forming a part of the first cyclone outlet.

19. A blood delivery system for delivering blood to a blood recipient, the blood having a blood phase and a gaseous phase, the blood delivery system comprising:
 a blood donor device for providing a source of blood; and
 a cyclone device according to claim 1 for receiving the blood from the blood donor device, separating the gaseous phase from the blood phase of the blood, and delivering the blood phase to the recipient.

20. The blood delivery system of claim 19, wherein the cyclone eddy chamber narrows at a narrow end, and the narrow end is proximate to both the first and second cyclone outlets.

21. The blood delivery system of claim 20, further comprising a diffuser section having first and second axial ends, the first axial end communicating with the narrow end of the cyclone eddy chamber, the diffuser section widening at the second axial end and forming a part of the first cyclone outlet.

* * * * *

UNITED STATES PATENT AND TRADEMARK OFFICE
Certificate

Patent No. 5,824,212　　　　　　　　　　　　　　　　　　　　Patented: October 20, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Alexander Brockhoff, Fürstentum, Liechtenstein; and Hans Plechinger, Christ Church, Barbados.

Signed and Sealed this Twenty-sixth Day of October 2004.

BENJAMIN L. UTECH
*Supervisory Patent Examiner*
Art Unit 1722